United States Patent [19]
Tritthart et al.

[11] Patent Number: 5,571,532
[45] Date of Patent: Nov. 5, 1996

[54] PHARMACEUTICAL PREPARATION FOR SUPPLYING FLUORIDE IONS

[75] Inventors: Wolfram Tritthart, Wolfsberg; Rudiger Wolf, Vienna, both of Austria

[73] Assignee: Asta Medica Arzneimittal Ges. m.b.H., Osterreich, Austria

[21] Appl. No.: 124,310

[22] Filed: Sep. 20, 1993

[30] Foreign Application Priority Data

Oct. 26, 1992 [DE] Germany ............ 42 36 090.0

[51] Int. Cl.$^6$ .................................................. A61K 9/20
[52] U.S. Cl. .................. 424/464; 424/490; 424/493; 424/495
[58] Field of Search ................ 424/464, 493, 424/422, 495, 490

[56] References Cited

U.S. PATENT DOCUMENTS

| | | | |
|---|---|---|---|
| 4,882,169 | 11/1989 | Ventouras | 424/493 |
| 5,071,655 | 12/1991 | Baylink | 424/422 |
| 5,082,662 | 1/1992 | Laurent et al. | 424/464 |
| 5,096,717 | 3/1992 | Wirth et al. | 424/490 |

*Primary Examiner*—Thurman K. Page
*Assistant Examiner*—William E. Benston, Jr.
*Attorney, Agent, or Firm*—Felfe & Lynch

[57] ABSTRACT

Pharmaceutical preparation in tablet form for supplying fluoride ions for the treatment and prevention of losses of bone substance, including osteoporosis and alveolar bond damage, with a content of sodium fluorophosphate and substances for regulating the release of sodium fluorophosphate, the substances for the regulation of the sodium fluorophosphate release comprising a dual retardant system which consists of a retardant matrix in the tablet core and a retardant coating.

14 Claims, 5 Drawing Sheets

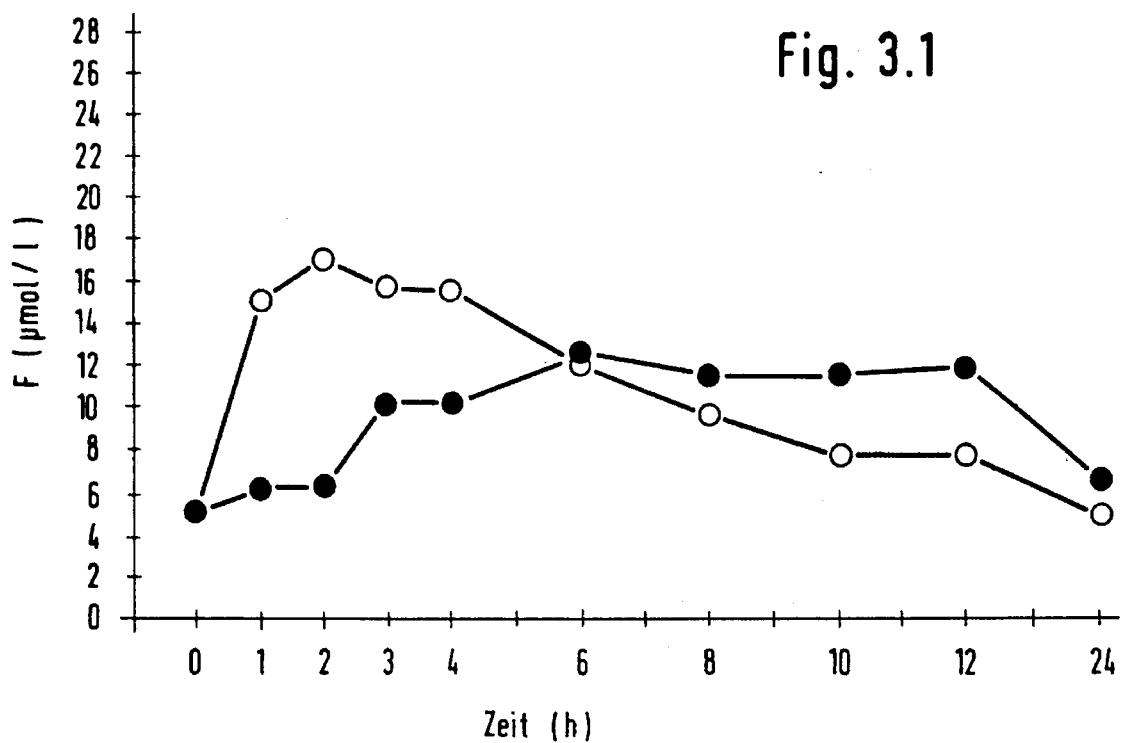
Fig. 3.1
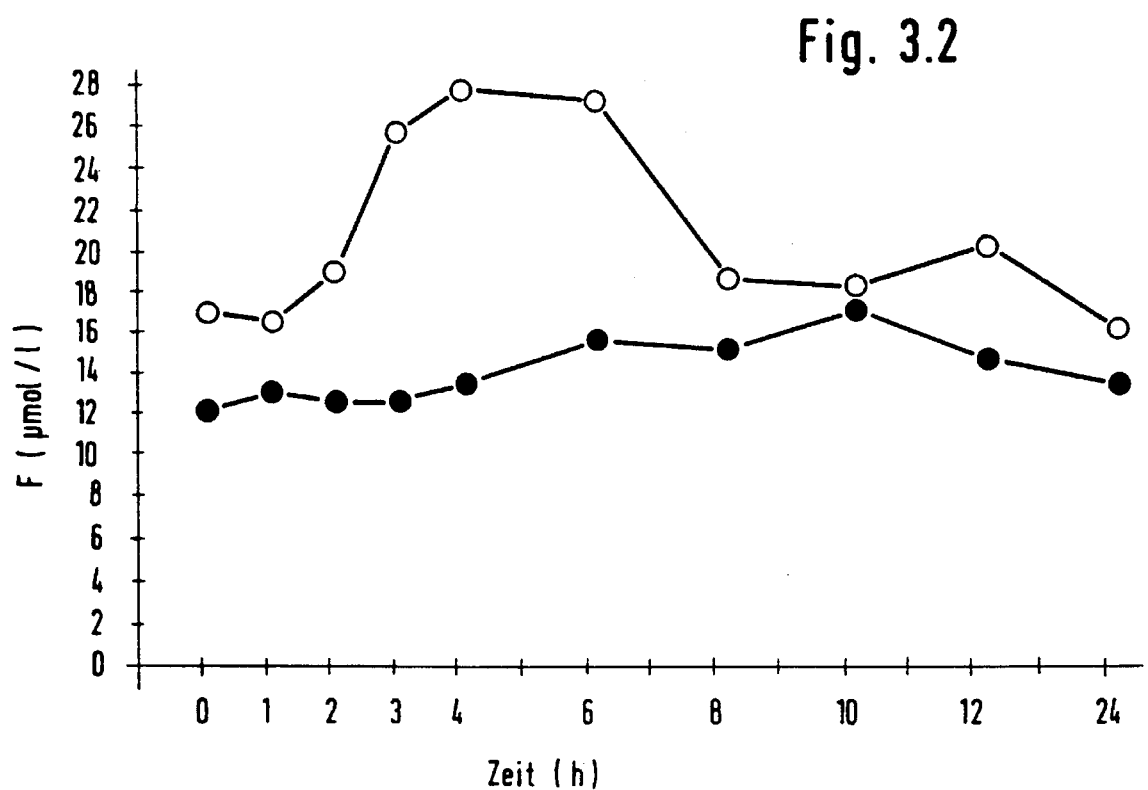
Fig. 3.2

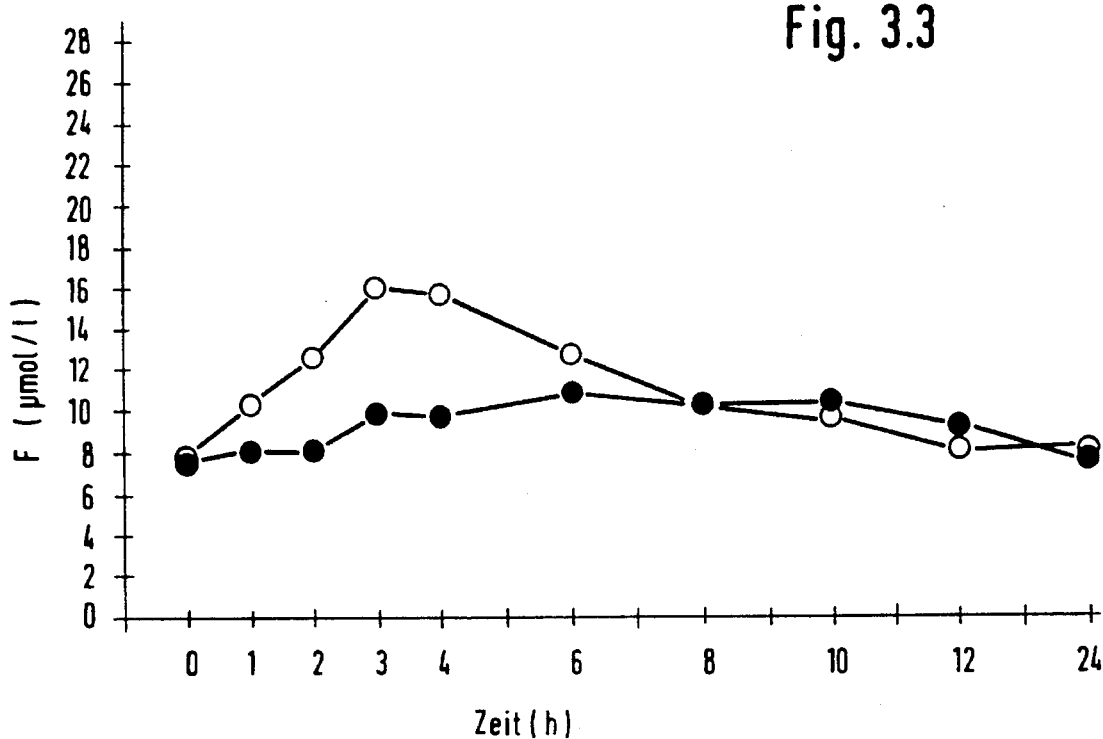
Fig. 3.3
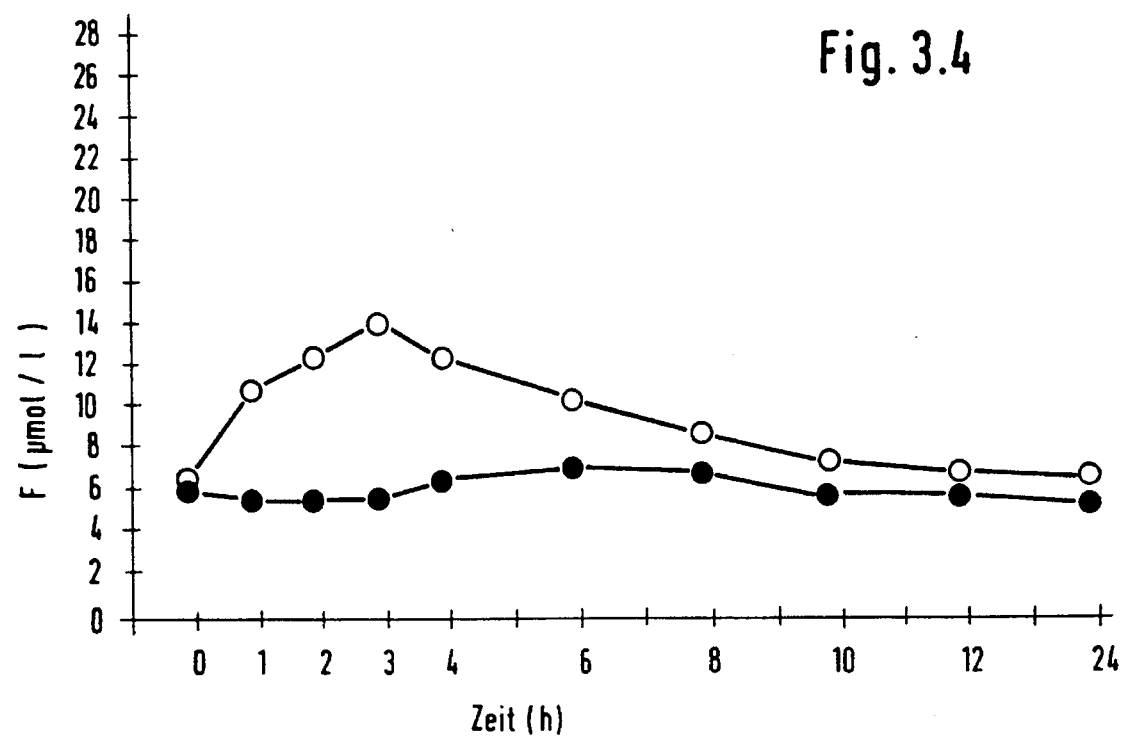
Fig. 3.4

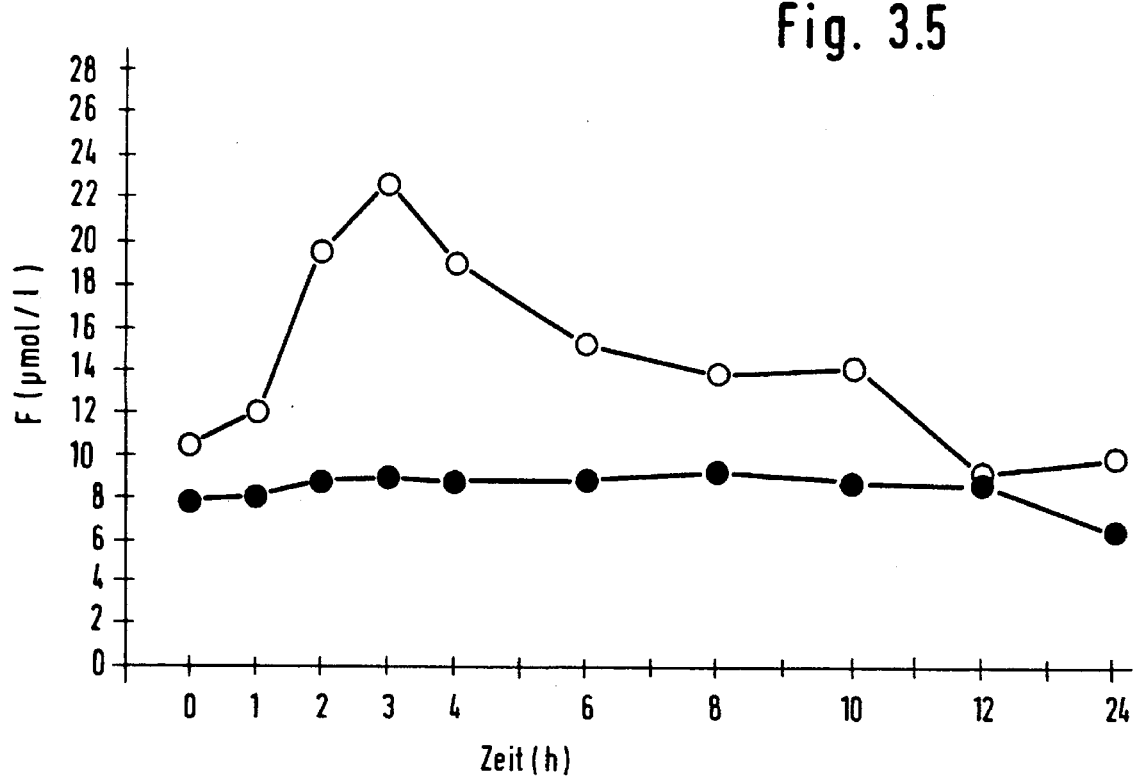
Fig. 3.5
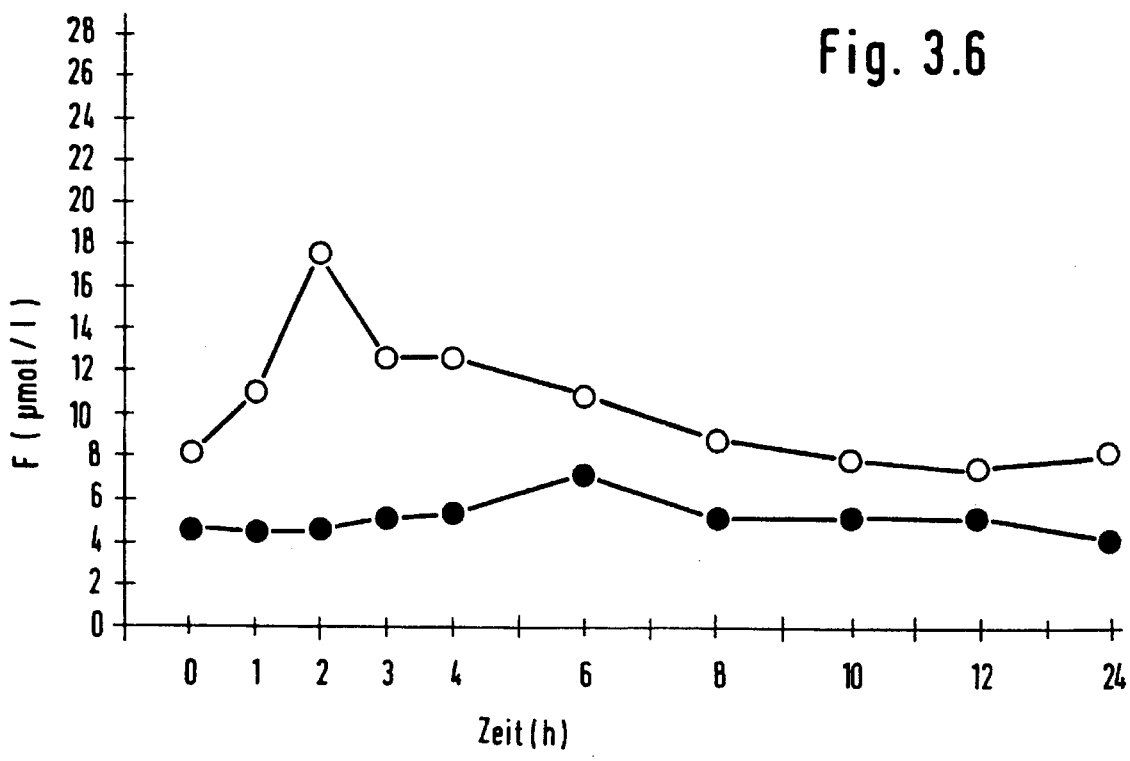
Fig. 3.6

PHARMACEUTICAL PREPARATION FOR SUPPLYING FLUORIDE IONS

The invention relates to a pharmaceutical preparation for supplying fluoride ions for the treatment and prevention of bone substance losses, including osteoporosis and alveolar bone damage, with a content of sodium fluorophosphate and of substances for regulating the release of sodium fluorophosphate.

It is known that fluorides stimulate the activity of bone-forming cells and is stored in the bone structure together with calcium and phosphate, the chief components of bone.

It is known, from U.S. Pat. No. 3,287,219, that the healing of bone can be improved by the oral administration of sodium fluoride.

Furthermore, the use of sodium fluoride or sodium fluorophosphate for the treatment of bone damage has been increasingly discussed in recent times. In Europe, for example, a tablet with a content of 22 mg of sodium fluoride corresponding to 10 mg of fluorine has been sold under the name "Flurexal" by the firm of Zyma S.A., of Nyon, Switzerland, and a chewable tablet with a content of 38 mg of sodium fluorophosphate corresponding to 5 mg of fluorine has been sold under the name "Tridin" by Opfermann Arzneimittel GmbH. "Flexural" is administered three times daily, and "Tridin," is administered in an amount of 1 to 2 tablets, three times daily, for the treatment of steroid osteoporosis, or one tablet three times daily.

The consumer information on "Tridin" indicates that gastric and intestinal irritation are observed only rarely. In Caries Res. 17 (Suppl. 1), pages 46 to 55 (1983), it is reported by Yngve Ericsson in "Monofluorophosphate Physiology: General Considerations" that neither in patients nor in numerous experiments with laboratory personnel have any subjective adverse effects been observed at doses up to 30 mg of fluorine as fluorophosphate. Clinical studies and patient reports in the meantime show, however, that gastric and intestinal disturbances occurred in a considerable number of cases.

To remedy these disadvantages, generic pharmaceutical preparations are described in German Patent Disclosure Documents 37 27 615 and 37 27 616 (in the case of 37 27 615 with an additional content of a composition containing calcium) in which substances for the release of sodium fluorophosphate, in the form of cellulose powder or cellose threads which swell in water, are proposed. These substances form a coherent network as a matrix in which the sodium fluorophosphate is uniformly and homogeneously dispersed, and after the regular form of the medication is put into an aqueous medium, the cellulose powder or the cellulose threads on the surface of the regular form soften and thus release part of the sodium fluorophosphate. This matrix is said to function such that the release of the fluorine is retarded or is very slow within the first 1 to 8 hours, so that the medication passes through the stomach and enters the intestinal tract before the uniform release occurs.

More precise studies have shown, however, that the release of the active substance is not linear. After 1 hour, 40% of the active substance has been released. After 5 hours, 70%. And after 6 hours, a plateau of 75% is reached. A release test in artificial gastric juices showed 2% free fluoride with respect to the entire medication form after 2 hours, which with respect to the total fluoride, corresponds to about 15.2%, a level which substantially is the same as the release of sodium fluorophosphate without a retarding system. This suggests a higher side-effect rate.

In vivo data prove these in vitro experiments. In the data on six patients, it was shown that a peak is reached in only 3 hours. The therapeutic aim of the known preparation, of achieving a controlled release of active substance over as long as 8 hours in vivo is not achieved. Also, the release of more than 50% of the fluorine takes place within the first hour.

It is therefore the object of the present invention to improve the known retarding system such that the release will be as linear as possible and take place at least beyond the period of time stated for the known preparation but not achieved thereby, of more than 8 hours.

This object is achieved according to the invention by the fact that the means for regulating the release of sodium fluorophosphate comprise a dual retarding system, which is made of a retardant matrix in the core of the tablet and a retardant coating.

It is preferred that the retardant matrix be based on copolymers of acrylic and methacrylic acid esters, polyvinyl acetate, ethylcellulose or a wax matrix.

The retardant matrix is preferably based on an aqueous dispersion of copolymers of acrylic and methacrylic acid esters with a small content of quaternary ammonium groups.

It is especially preferred to base the retardant matrix on a mixture of Eudragit® RSPM (poly(ethyl acrylate, methyl methacrylate, trimethylammonioethyl methacrylate chloride) 1:2:0.1, 150 000); and Eudragit® RS30D (poly(ethyl acrylate, methyl methacrylate, trimethylammonioethyl methacrylate chloride) 1:2:0.1, 150 000, polyacrylate dispersion 30 per cent, Eudragit® RSPM and Eudragit® RS30D being contained preferably in a ratio of about 4:1 to 1:1.

The invention proposes that the retardant coating be based on copolymers of acrylic and methacrylic acid esters, ethyl cellulose or films resistent to gastric juices, such as hydroxypropylmethylcellulosephthalate or shellac.

Preferably the retardant coating is based on an aqueous dispersion of copolymers of acrylic and methacrylic acid esters with a small content of quaternary ammonium groups, the retardant coating being based with special preference on Eudragit® RS30D.

Following composition dissolved:

| Core: | Sodium fluorophosphate | 79.80 mg |
|---|---|---|
| | Eudragit® RSPM | 63.55 mg |
| | Eudragit® RS 30 D | 25.50 mg |
| | Magnesium stearate | 3.00 mg |
| | Boeson® VP | 3.00 mg |
| | Stearic acid powder | 4.00 mg |
| | Aerosil 200 | 1.00 mg |
| Coating: | Talc | 2.90 mg |
| | Titanium dioxide | 2.05 mg |
| | Diethylphthalate | 0.34 mg |
| | Eudragit® RS 30 D | 5.70 mg |

According to the invention, a content of 120 to 200 mg of sodium fluorophosphate is provided in the case of a formulation to be administered daily or a content of 40 to 100 mg of sodium fluorophosphate in the case of a formulation to be administered twice daily.

The present invention succeeds for the first time in effectively overcoming the disadvantages of the state of the art. This has been achieved by the novel dual retarding system which in the core consists preferably of copolymers of acrylic and methacrylic acid esters, but alternatively can also be made on the basis of polyvinyl acetate, ethyl cellulose or wax matrix. In these materials it is also of especial importance that they permit manufacture without organic solvents, which in view of the usual retardants, namely acrylic varnish resin substances dissolved in organic solvent, represents a significant advantage.

Additional components in the core can be Aerosil as a flow agent and magnesium stearate, Boeson VP® and stearic acid as lubricant and parting agent.

Another important element—in addition to the special character of the retardant matrix—of the present invention with respect to German Patent Disclosure Document 37 27 616, is the provision of an additional retardant coating, which is also preferably based on copolymers of acrylic and methacrylic acid esters, and can additionally contain talc as lubricant, titanium dioxide as pigment, and diethylphthalate as plasticizer. In addition, ethylcellulose films can be used as enveloping agents, but also films resistant to gastric juices, such as hydroxymethylcellulosephthalate or shellac, for example.

The combination of the retardant matrix according to the invention and a coating configured as a diffusion membrane leads to an unforeseeable superadded slowing of the release of sodium fluorophosphate, and therefore makes it possible for the first time to achieve the release of the active substance and an active-substance plateau in the periods of time desired.

Surprisingly, it has been found that the novel pharmaceutical preparation can provide the desired action as regards the release of fluoride. The release of the active substance takes place in the case of the once-a-day formulation in a period of 8.5 to 12 hours, while in the case of the twice-a-day formulation it takes place in a period of 5 to 8 hours. It has been found that in the artificial gastric juice, less than 1% of free fluoride, with respect to the total sodium fluorophosphate, is released in 2 hours, so that gastrointestinal side effects are effectively prevented. The novel pharmaceutical preparation achieves an effective substance plateau in vivo of 10 to 18 hours with the one-a-day formulation and of 6 to 12 hours with the twice-a-day formulation.

The experiments performed in vivo and in vitro with a special embodiment of the preparation according to the invention are explained in detail with the appended drawings.

Figure 1:
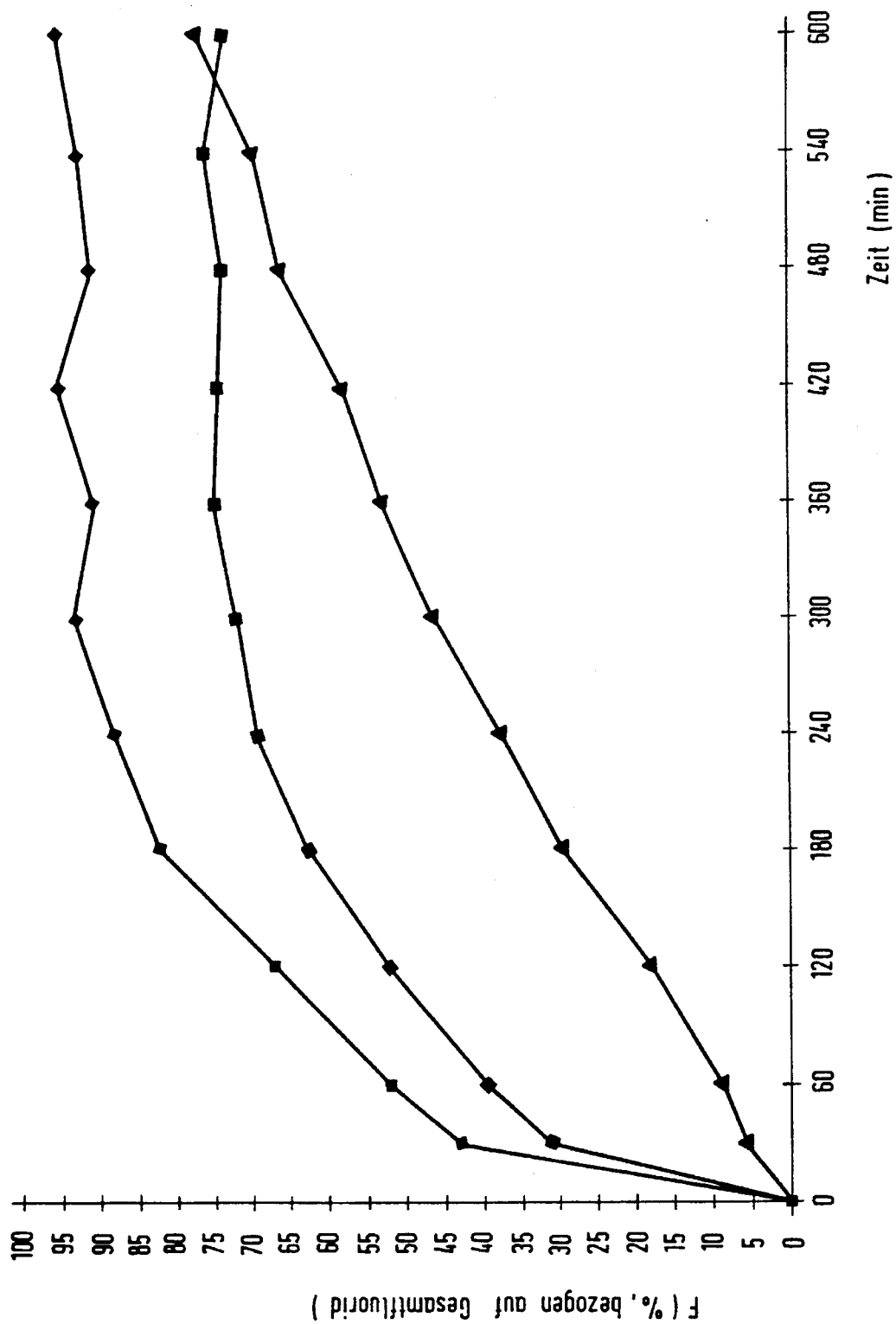
FIG. 1 shows a graph containing curves for the release of active substance in three different preparations.

In FIG. 1, three different release curves for various preparations containing sodium fluorphosphate are represented, the percentage data plotted on the vertical representing the accumulative release of sodium fluorophosphate, and on the horizontal the time in minutes.

The upper curve shows the release profile for tablets in accordance with German Patent Disclosure Document 37 27 616. The middle curve is the release profile for a tablet with a retardant matrix according to the invention, but without the additional coating. Lastly, the bottom curve is the release profile of a tablet with the dual retardant system of the invention. As it can be seen, it is only with the combination in accordance with the invention of a retardant matrix and a retardant coating that a substantially linear release of sodium fluorophosphate is achieved, approximately 8% being released in one hour and about 42% in 6 hours. The release profile represented was measured on a tablet which contains 152 mg of sodium fluorophosphate and is intended for once-a-day administration (sustained release for 8 to 10 hours). Ideal for twice-daily administration is a 76 mg formulation which has a similar release profile (sustained release for 6 to 8 hours).

Figure 2:
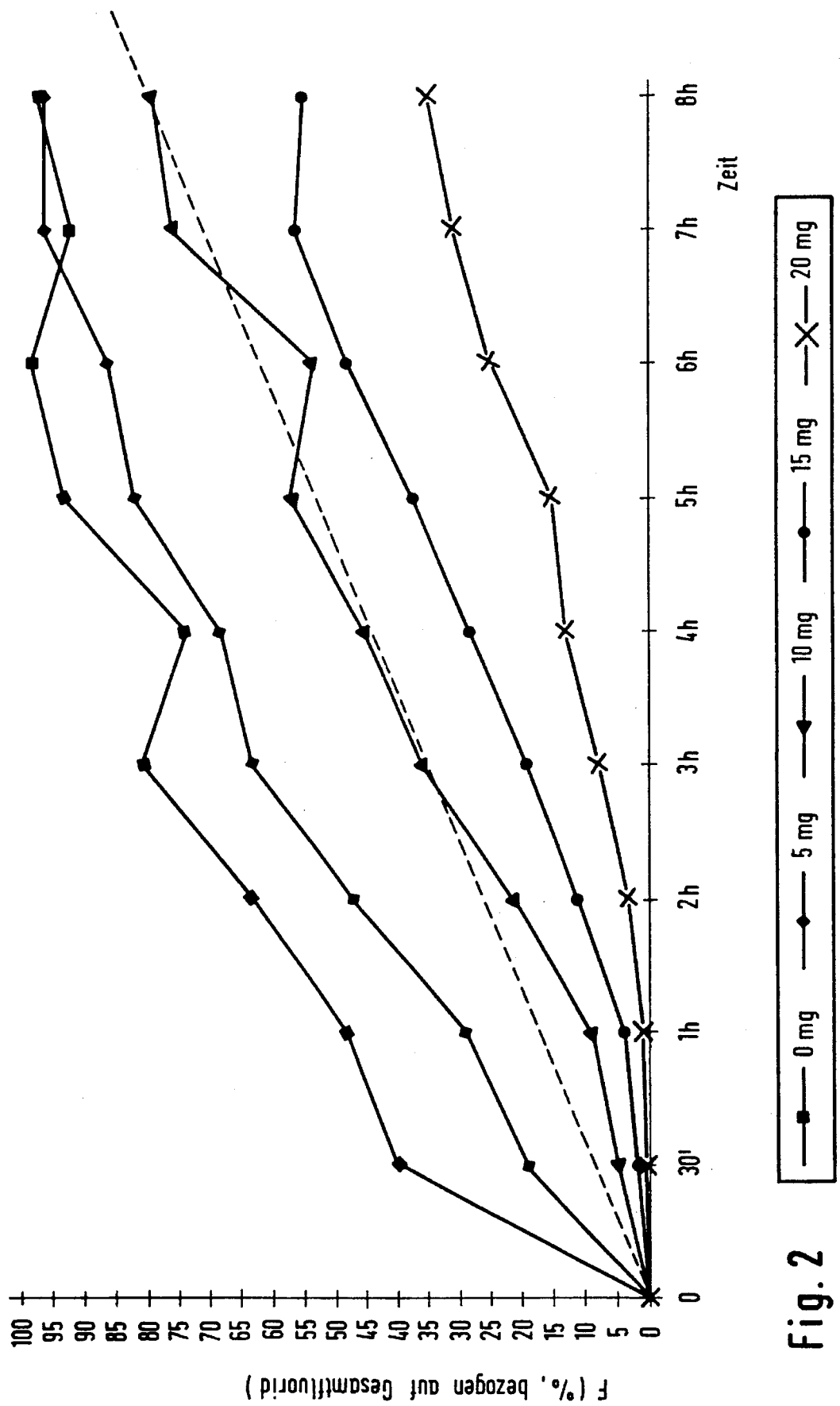
FIG. 2 shows a graph containing curves showing the release of active substance from tablets with film coatings of various thickness, and FIGS. 3.1–3.6 are fluoride profiles of six different osteoporosis patients over 24 hours, who had been treated with the known preparation and with the preparation according to the invention.

FIG. 2 shows the release profile of tablets which in any case contain the retardant matrix according to the invention but have film coatings of different thickness, as given. The release profiles were measured in artificially formulated gastric juice, and after two hours in artificially produced intestinal juice.

The diagram shows that the rate of release is substantially directly proportional to the film thickness, a film coating of 10 mg being especially preferred on account of the substantially linear release. In contrast to the release in the case of a tablet according to the state of the art, the more greatly sustained and linear release obtained with the dual retardant system according to the invention indicates a substantial reduction of the gastrointestinal side effects.

The in vitro experiments represented were supported by additional in vivo experiments. In FIGS. 3.1–3.6, 24-hour fluoride profiles of six female osteoporosis patients, the fluoride concentration in μmol/l being recorded on the ordinates and the time in hours on the abscissas. The release profiles with the open dots correspond to the administration of a sodium fluorophosphate preparation according to the state of the art, while the release profiles with the solid dots correspond to the administration of the preparation according to the invention. In all cases, a decidedly slower release can clearly be discerned especially in the first six hours, which effectively contributes to reducing the gastrointestinal side effects in the patients.

EXAMPLE OF MANUFACTURE

For a batch of 100,000 film-coated tablets according to the invention, the following raw materials are needed in the following amounts:

| Core: | Sodium fluorophosphate | 7.980 kg |
|---|---|---|
| | Eudragit ® RSPM | 6.355 kg |
| | Eudragit ® RS 30 D | 2.550 kg |
| | Magnesium stearate | 0.300 kg |
| | Boeson ® VP | 0.300 kg |
| | Stearic acid powder | 0.400 kg |
| | Aerosil 200 | 0.100 kg |
| Coating: | Talc | 0.290 kg |
| | Titanium dioxide | 0.205 kg |
| | Diethylphthalate | 0.034 kg |
| | Eudragit ® RS 30 D | 0.570 kg |

One lacquered tablet thus contains:

| Core: | Sodium fluorophosphate | 79.80 mg |
|---|---|---|
| | Eudragit ® RSPM | 63.55 mg |
| | Eudragit ® RS 30 D | 25.50 mg |
| | Magnesium stearate | 3.00 mg |
| | Boeson ® VP | 3.00 mg |
| | Stearic acid powder | 4.00 mg |
| | Aerosil 200 | 1.00 mg |
| Coating: | Talc | 2.90 mg |
| | Titanium dioxide | 2.05 mg |
| | Diethylphthalate | 0.34 mg |
| | Eudragit ® RS 30 D | 5.70 mg |

Common galenic techniques can be used in manufacture.

The features disclosed in the above description and in the claims and the appended drawings may be important both individually and in any combination for the realization of the invention in its various embodiments.

We claim:

1. A tablet for the treatment and prevention of bone loss which facilitates a substantially linear release of sodium fluorophosphate, said tablet comprising an effective amount of sodium fluorophosphate, a hydrophobic retardant core matrix and a retardant coating, wherein said hydrophobic retardant core matrix is selected from the group consisting of copolymers of acrylic and methacrylic acid esters, polyvinyl acetate, ethylcellulose and a wax matrix, said retardant coating being selected from the group consisting of copolymer of acrylic and methacrylic acid esters, ethylcellulose, and films resistant to gastric juices.

2. A tablet according to claim 1, wherein said hydrophobic retardant core matrix further comprises an aqueous dispersion of said copolymers and quaternary ammonium groups.

3. A tablet according to claim 2, wherein in said hydrophobic retardant core matrix comprises a mixture of Eudragit® RSPM and Eudragit® RS30D.

4. A tablet according to claim 3, wherein said Eudragit® RSPM and Eudragit® RS30D are present in a ratio ranging from about 4:1 to about 1:1.

5. A tablet according to claim 1 wherein said film resistant to gastric juices comprises hydroxypropylmethylcellulosephthalate.

6. A tablet according to claim 1 wherein said film resistant to gastric juices comprises shellac.

7. A tablet according to claim 1, wherein said retardant coating further comprises an aqueous dispersion of said copolymers and quaternary ammonium groups.

8. A tablet according to claim 7, wherein said retardant coating comprises Eudragit® RS30D.

9. A tablet according to claim 1, wherein said tablet contains 120 to 200 mg of sodium fluorophosphate.

10. A tablet according to claim 1, wherein said tablet contains 40 to 100 mg of sodium fluorophosphate.

11. A tablet according to claim 1, comprising:

| | | |
|---|---|---|
| Core: | Sodium fluorophosphate | 79.80 mg |
| | Eudragit ® RSPM | 63.55 mg |
| | Eudragit ® RS 30 D | 25.50 mg |
| | Magnesium stearate | 3.00 mg |
| | Boeson ® VP | 3.00 mg |
| | Stearic acid powder | 4.00 mg |
| | Aerosil 200 | 1.00 mg |
| Coating: | Talc | 2.90 mg |
| | Titanium dioxide | 2.05 mg |
| | Diethylphthalate | 0.34 mg |
| | Eudragit ® RS 30 D | 5.70 mg. |

12. A method for treating osteoporosis comprising administering to a patient an effective amount of the tablet of claim 1.

13. A method for treating osteoporosis according to claim 12, wherein said tablet contains from about 120 to about 200 mg of sodium fluorophosphate and is administered daily.

14. A method for treating osteoporosis according to claim 12, wherein a tablet contains from about 40 to about 100 mg of sodium fluorophosphate and is administered twice daily.

* * * * *